(12) United States Patent
Yoshimura et al.

(10) Patent No.: US 11,609,190 B2
(45) Date of Patent: Mar. 21, 2023

(54) NON-DESTRUCTIVE INSPECTION METHOD

(71) Applicants: Topcon Corporation, Tokyo (JP); RIKEN, Wako (JP)

(72) Inventors: Yuichi Yoshimura, Tokyo (JP); Maki Mizuta, Wako (JP); Hideyuki Sunaga, Wako (JP); Yoshie Otake, Wako (JP)

(73) Assignees: Topcon Corporation, Tokyo (JP); RIKEN, Wako (JP)

( * ) Notice: Subject to any disclaimer, the term of this patent is extended or adjusted under 35 U.S.C. 154(b) by 238 days.

(21) Appl. No.: 17/041,963

(22) PCT Filed: Sep. 27, 2018

(86) PCT No.: PCT/JP2018/036018
§ 371 (c)(1),
(2) Date: Sep. 25, 2020

(87) PCT Pub. No.: WO2019/187235
PCT Pub. Date: Oct. 3, 2019

(65) Prior Publication Data
US 2021/0131981 A1 May 6, 2021

(30) Foreign Application Priority Data
Mar. 28, 2018 (JP) .............................. JP2018-062046

(51) Int. Cl.
*G01N 23/05* (2006.01)
*G01N 23/02* (2006.01)
(Continued)

(52) U.S. Cl.
CPC ........... *G01N 23/05* (2013.01); *G01N 23/025* (2013.01); *G01N 23/09* (2013.01); *G01N 33/383* (2013.01);
(Continued)

(58) Field of Classification Search
CPC ...... G01N 23/05; G01N 23/025; G01N 23/09; G01N 33/383; G01N 2223/04; G01N 2223/106; G01N 2223/409; G01N 2223/60
See application file for complete search history.

(56) References Cited

U.S. PATENT DOCUMENTS 10,690,802 B2 * 6/2020 Stoller .................... E21B 33/14
2017/0167243 A1 6/2017 Guo et al.

FOREIGN PATENT DOCUMENTS

EP 3066301 A1 9/2016
JP 4-15508 A 1/1992
(Continued)

OTHER PUBLICATIONS

Yoshimura et al., "Measurement of Water in Concrete by a Compact Accelerator-Driven Neutron Source," Oct. 12, 2017, pp. 1-6.
(Continued)

*Primary Examiner* — David P Porta
*Assistant Examiner* — Fani Polyzos Boosalis
(74) *Attorney, Agent, or Firm* — Chiesa Shahinian & Giantomasi PC (57) ABSTRACT

The non-destructive inspection method includes: a water absorbing or drying step of changing a water-content state of a test piece; a transmission image capturing step of irradiating, with a radiation, the test piece absorbed water or dried for a predetermined time in the water absorbing or drying step and capturing a transmission image created by visualizing the radiation transmitted through the test piece; and an evaluation step of evaluating the test piece on the basis of the water-content state of the test piece determined from the transmission image captured in the transmission image capturing step.

16 Claims, 10 Drawing Sheets

(51) Int. Cl.
    *G01N 23/09*     (2018.01)
    *G01N 33/38*     (2006.01)
(52) U.S. Cl.
    CPC ... *G01N 2223/04* (2013.01); *G01N 2223/106* (2013.01); *G01N 2223/409* (2013.01); *G01N 2223/60* (2013.01)

(56) References Cited

FOREIGN PATENT DOCUMENTS

| JP | H10-227735 A | | 8/1998 |
|----|---|---|---|
| JP | H11-51880 A | | 2/1999 |
| JP | 2000-105205 A | | 4/2000 |
| JP | 2000105205 A | * | 4/2000 |
| JP | 2018-028438 A | | 2/2018 |
| MX | 2016006374 A | | 12/2016 |
| WO | 2015102574 A1 | | 7/2015 |

OTHER PUBLICATIONS

Kanematsu, "Visualization of moisture in concrete by neutrons", Concrete Engineering, 2015, vol. 53, 18 pgs, including translation.
Notice of Reasons for Refusal dated May 10, 2022, in connection with Japanese Patent Application No. 2018-062046, 6 pgs, including translation.
International Search Report and Written Opinion dated Dec. 4, 2018, in connection with International Patent Application No. PCT/JP2018/036018, filed Sep. 27, 2018, 9 pgs [including translation].
Tetsu-to-Hagane, "Non-Destructive Inspection of Under-Film Corroded Steels using a Compact Neutron Source," Mar. 2014, vol. 100, No. 3, pp. 429-431 [partial translation attached].

* cited by examiner

| NAME | EXPANSION AMOUNT DURING TEST (μ) | ALKALI AMOUNT (kg/m³) | MIXING AMOUNT | | | | | | | | |
|---|---|---|---|---|---|---|---|---|---|---|---|
| | | | W/C (%) | s/a (%) | Gmax (mm) | UNIT AMOUNT (kg/m³) | | | | | AE AGENT |
| | | | | | | W | C | S | G | | |
| N | - | - | 50 | 45.1 | 20 | 184 | 368 | 779 | 973 | | 4.05 |
| ASR300a | 310 | 3 | 55 | 44.5 | 20 | 168 | 305 | 786 (30kg) | 980 | | 0.16 |
| ASR300b | 350 | 5 | | | | | | 786 (30kg) | | | |
| ASR900a | 875 | 8 | | | | | | 786 (30%) | | | |
| ASR900b | 930 | | | | | | | 786 (30%) | | | |

FIG.5

| TEST PIECE | EXPANSION AMOUNT ($\mu$) | POROSITY MEASURED WITH X-RAY CT (%) | ULTRASOUND PROPAGATION VELOCITY (m/s) | | |
|---|---|---|---|---|---|
| | | | WATER-SATURATED STATE | DRIED STATE | (WATER-SATURATED STATE) −(DRIED STATE) |
| N | − | 9.2 | 5095 | 4759 | 336 |
| ASR300a | 300 | 5.4 | 4657 | 4324 | 333 |
| ASR300b | 350 | 5.2 | 4586 | 4330 | 256 |
| ASR900a | 1000 | 8.7 | 4588 | 4250 | 338 |
| ASR900b | 950 | 9.1 | 4478 | 4078 | 400 |

NON-DESTRUCTIVE INSPECTION METHOD

CROSS-REFERENCE TO RELATED APPLICATIONS

This application is a national stage under 35 U.S.C. § 371 of International Patent Application No. PCT/JP2018/036018, filed Sep. 27, 2018, which claims priority to Japanese Patent Application No. 2018-062046, filed Mar. 28, 2018, the disclosures of both are incorporated herein by reference in their entirety.

TECHNICAL FIELD

The present disclosure relates to a non-destructive inspection method by which a non-destructive inspection is performed on a test piece with radiation.

BACKGROUND ART

In recent years, it has been desired to appropriately maintain, repair, or renew aging infrastructures (hereinafter, referred to as infrastructure constructions) such as roads, bridges, tunnels, and building structures.

In particular, in the case of concrete structures, there are possibilities of a volume change (expansion or contraction) caused under influence of materials and environments and of causing a defect such as a crack.

To address this problem, in a conventional evaluation of expansion/contraction amount of concrete, pins are embedded or bonded at two positions, a distance between the two positions of the pins is measured on a regular basis with a contact gauge or the like, and an expansion amount is calculated from an amount of change in the distance. However, in this evaluation technique, when the distance between the positions of the two pins changes largely, there is a possibility that the pins come off, so that the evaluation may not be performed. Further, there is a problem in that it is impossible to evaluate a portion where no pins are present. Therefore, a method for evaluating concrete structures by a non-destructive inspection is desired.

For example, in Patent Document 1, a radiation source for emitting a neutron ray is provided on one external surface at a corner part of a concrete wall, and a neutron detector for receiving the neutron ray emitted from the radiation source is provided on the other external surface, to detect a water content of the concrete wall. Then, a degree of deterioration of the concrete wall is evaluated from the detected water content.

CITATION LIST

Patent Document

Patent Document 1: Japanese Unexamined Patent Publication No. 2018-28438

SUMMARY OF THE INVENTION

Technical Problem

However, Patent Document 1 does not specifically describe how the deterioration of the concrete wall is evaluated from the water content of the concrete wall detected by using a neutron ray. Therefore, required is a technique for accurately evaluating deterioration of a measurement object on the basis of a water content of the measurement object.

In view of the above, an embodiment of the present invention is made to solve such a problem, and an object of the embodiment is to provide a non-destructive inspection method that can more accurately evaluate the deterioration of a test piece on the basis of a water-content state of the test piece.

Solution to the Problem

In order to achieve the above object, a non-destructive inspection method according to an embodiment of the present invention includes: a water absorbing or drying step of changing a water-content state of a test piece; a transmission image capturing step of irradiating, with a radiation, the test piece that has been subjected to absorption or drying for a predetermined time in the water absorbing or drying step and capturing a transmission image created by visualizing the radiation transmitted through the test piece; and an evaluation step of evaluating the test piece, based on the water-content state of the test piece determined from the transmission image captured in the transmission image capturing step.

In this non-destructive inspection method, the test piece may be concrete.

In this non-destructive inspection method, the radiation used in the transmission image capturing step may be neutron.

In this non-destructive inspection method, the water-content state of the test piece determined from the transmission image in the evaluation step may include non-uniformity of a water permeation height.

The water-content state of the test piece determined from the transmission image in the evaluation step may include a variation of a permeation rate into the test piece.

The water-content state of the test piece determined from the transmission image in the evaluation step may include a time differential of a water absorption rate of the test piece.

Advantages of the Invention

The embodiment of the present invention using the above-described means can more accurately evaluate the deterioration of a test piece on the basis of the water-content state of the test piece.

DESCRIPTION OF EMBODIMENTS

An embodiment of the present disclosure will be described in detail with reference to the drawings.

Figure 1:
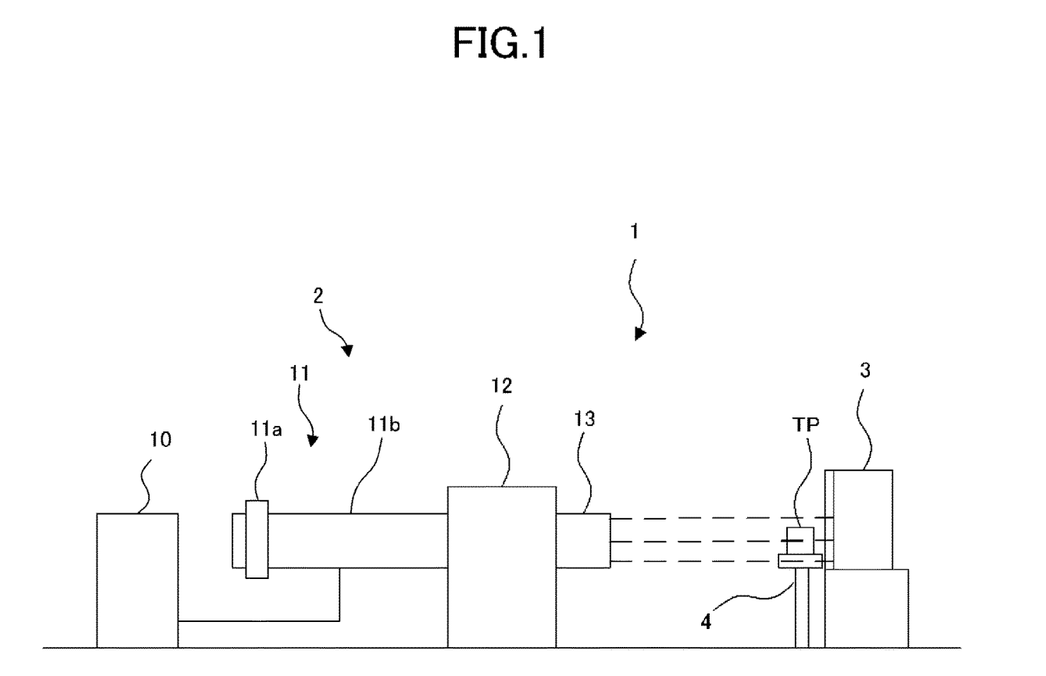
FIG. 1 is a schematic view illustrating a configuration of an inspection device used for a non-destructive inspection method according to the present embodiment.

FIG. 1 is a schematic view illustrating a configuration of an inspection device used for a non-destructive inspection method according to the present embodiment, and a configuration of the inspection device will be described below with reference to the drawing.

An inspection device 1 used in the non-destructive inspection method of the present embodiment includes a compact accelerator-driven neutron source 2, a detector 3, and a test piece support 4.

The compact accelerator-driven neutron source 2 includes: a power supply 10; a linear accelerator 11; and a target station 12 that serve as a radiation source; and an irradiator 13 that applies generated neutrons.

Specifically, the power supply 10 is a high-voltage power supply that supplies electric power to the accelerator. In one preferred embodiment, the high-voltage power supply of the power supply 10 has a power generation performance capable of accelerating at least protons to energy required for generation of neutrons, and a voltage fluctuation of the high-voltage power supply is small.

The linear accelerator 11 includes an ion source 11a and an accelerator 11b in a cylindrical shape extends from the ion source 11a and is connected to the target station 12.

The target station 12 is covered with a shield, and a target (not shown) for generating neutrons is provided inside the target station 12. The shield is made of a material that blocks neutrons and a gamma ray, and is, for example, made of lead or polyethylene containing boron. The target generates neutrons when colliding with protons, and can be, for example, beryllium (Be).

The irradiator 13 is made of polyethylene, which is a shield material, and applies neutrons (neutron beam) emitted from the target to a test piece TP.

The detector 3 includes an imaging system (imaging camera) that creates an image of an intensity distribution of neutrons, and outputs a transmission image of neutrons by converting a neutron ray into visible light with a neutron converter on the input side and imaging the visible light with an image sensor. The imaging camera may include a device such as an intensifier that amplifies an input signal.

The test piece support 4 is disposed close to the detector 3 to support the test piece TP to be located in front of an input surface of the detector 3. The test piece TP is a concrete piece, for example.

In the inspection device 1 configured as described above, for example, protons generated by the linear accelerator 11 and having energy of 7 MeV are brought to collide with beryllium located on the target station 12 to generate high-speed neutrons having maximum energy of 5 MeV. The high-speed neutrons are then passed through a polyethylene moderator to generate thermal neutrons of 50 MeV and high-speed neutrons of 1 MeV, and a neutron beam is outputted through the irradiator 13. Then, the test piece TP disposed on the test piece support 4 is irradiated with the neutron beam, and the number of neutrons passed through is measured by the detector 3, to visualize a spatial distribution of substances that absorbs and diffuses neutrons (capturing of a transmission image). In the present embodiment, thermal neutrons having energy on the scale of MeV are detected. Then, hydrogen having a large reaction cross section, i.e., water permeated is evaluated as the difference in neutron transmittance to concrete before and after water absorption.

Figure 2:
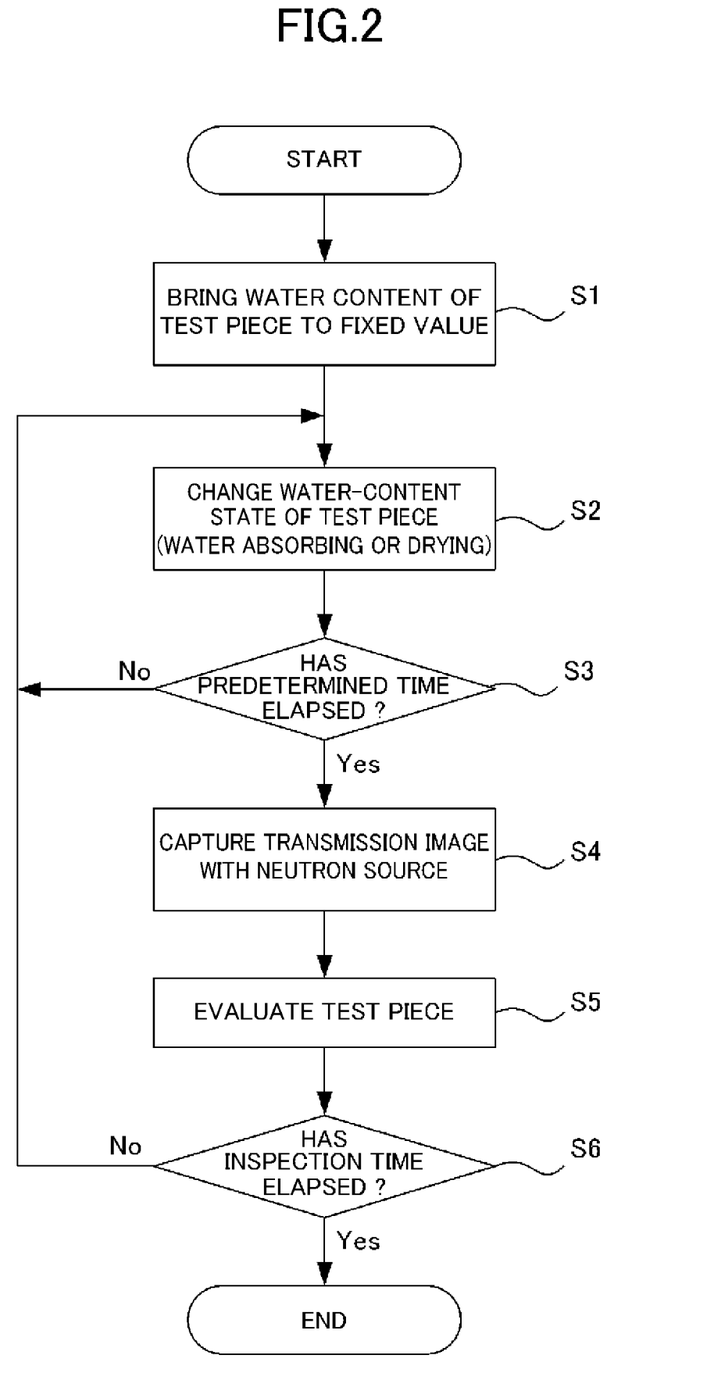
FIG. 2 is a flowchart of the non-destructive inspection method in the present embodiment.

FIG. 2 is a flowchart of the non-destructive inspection method in the present embodiment, and processes of the non-destructive inspection method will be described in accordance with the flowchart.

First, in step S1 of the present inspection method, a test piece TP is dried until its water content becomes a fixed value. The test piece TP may be dried in a humidistat bath or a furnace.

Figure 3:
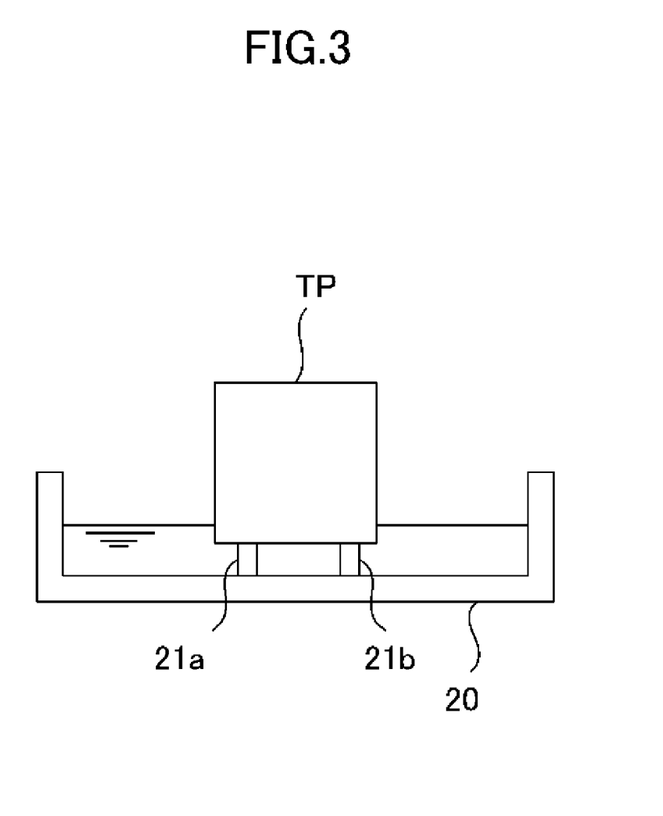
FIG. 3 is a schematic view of a water absorbing step on a test piece in the present embodiment.

Next, in step S2, a water-content state of the test piece TP is changed (water absorbing or drying step). For example, as shown in the schematic view of FIG. 3 illustrating the water absorbing step on the test piece TP, in the water absorbing or drying step, aluminum square bars 21a and 21b are provided on a bottom surface of an aluminum container 20 so that the test piece TP is not in direct contact with the bottom surface, and the test piece TP is placed on the aluminum square bars 21a and 21b. In addition, water is poured up to a few percent above the bottom of the test piece TP, thereby making the test piece TP absorb water through the bottom surface. Alternatively, the test piece TP is dried without pouring water.

Next, in step S3, it is determined whether a predetermined time set in advance has elapsed since the test piece TP absorbed water or is dried in step S2. As the predetermined time, few hours to several dozen hours are set, for example. If the result of the determination is false (No), the flow goes back to step S2, and the test piece TP is continued to absorb water or be dried. If the result of the determination is true (Yes), the flow proceeds to step S4.

In step S4, the compact accelerator-driven neutron source 2 is used to capture a transmission image of the test piece TP (transmission image capturing step). At the time of capturing the transmission image, the test piece TP is taken out from the aluminum container 20 and is weighed, placed on the test piece support 4, and irradiated with a neutron beam for a certain period of time (e.g., three minutes), to capture a transmission image.

In step S5, the test piece TP is evaluated (evaluation step). A degree of deterioration of the test piece TP such as a concrete piece depends on a volume change (expansion and contraction), and the volume change correlates with a water-content state of the test piece TP. In view of the above, the test piece TP is evaluated on the basis of the water-content state of the test piece TP that is determined from the transmission images captured at predetermined time intervals in step S4. Examples of the water-content state include water permeation properties such as a water permeation height, and a water permeation rate. This non-uniformity (variation) of the water content correlates with the expansion amount. The examples of the water-content state of the test piece TP further include a time differential of a water absorption rate.

Then, in the evaluation of the test piece TP in step S5, the water-content states of a plurality of test pieces cut out from the same block in the water absorbing or drying process are compared to estimate and evaluate the expansion amount on the basis of the non-uniformity of the water-content states. Regarding non-uniformity of the water-content state, in one preferred embodiment, a database is established in advance on a correlation between the non-uniformity of the water-content state of a model test piece and the expansion amount.

Next, in step S6, it is determined whether the inspection time determined in advance has elapsed. The inspection time is set to, for example, several hundred hours (several days), and if the inspection time has not yet elapsed, the result of the determination is false (No), and the flow goes back to step S2 to resume water absorption or drying. On the other hand, if the inspection time has elapsed, the result of the determination is true (Yes), and the evaluation is finished.

The water-content state of the test piece TP is determined from the transmission images created using the neutron source while the water-content state of the test piece is being changed, and the test piece TP is evaluated from the water-content state in the manner described above. Thus, the state of the test piece TP can be evaluated without damaging the test piece TP and, in addition, the state of the entire test piece TP can be evaluated in detail.

Further, the non-destructive inspection method according to the present embodiment is particularly suitable for concrete whose degree of deterioration changes depending on the water-content state.

Further, the use of neutrons as a radiation to capture transmission images allows the water-content state inside the test piece TP to be accurately detected.

Further, the use of non-uniformity of water permeation height or non-uniformity of water permeation rate as the water-content state of the test piece TP allows the expansion amount (or contraction amount) of the test piece TP to be accurately determined and deterioration to be determined highly accurately.

As described above, the non-destructive inspection method according to the present embodiment can more accurately evaluate the deterioration of the test piece TP.

Next, the following describes an example of the non-destructive inspection method of the present invention by which a correlation between the water permeation properties and the expansion amount for a concrete piece as a test piece TP can be determined.

Figure 4:
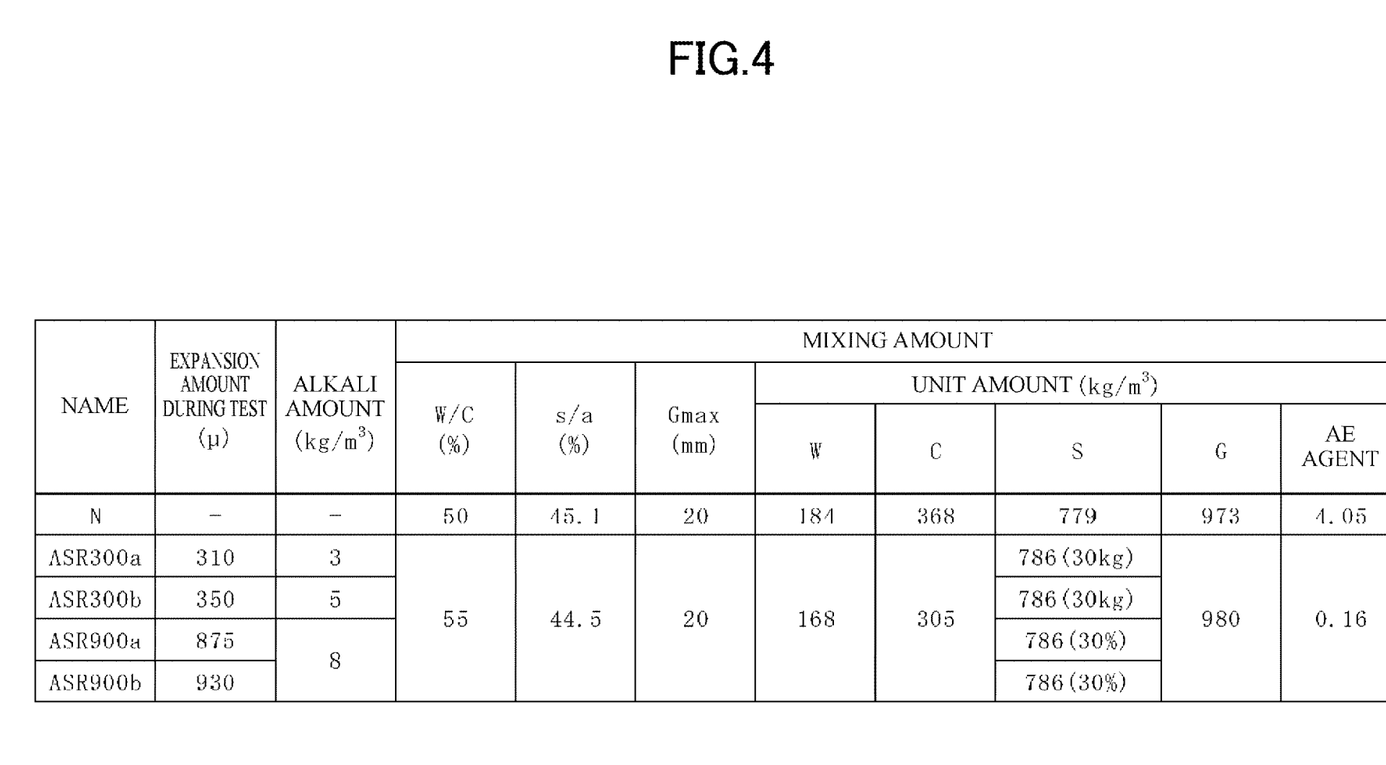
FIG. 4 is a list of test pieces used in the present embodiment.
Figure 5:
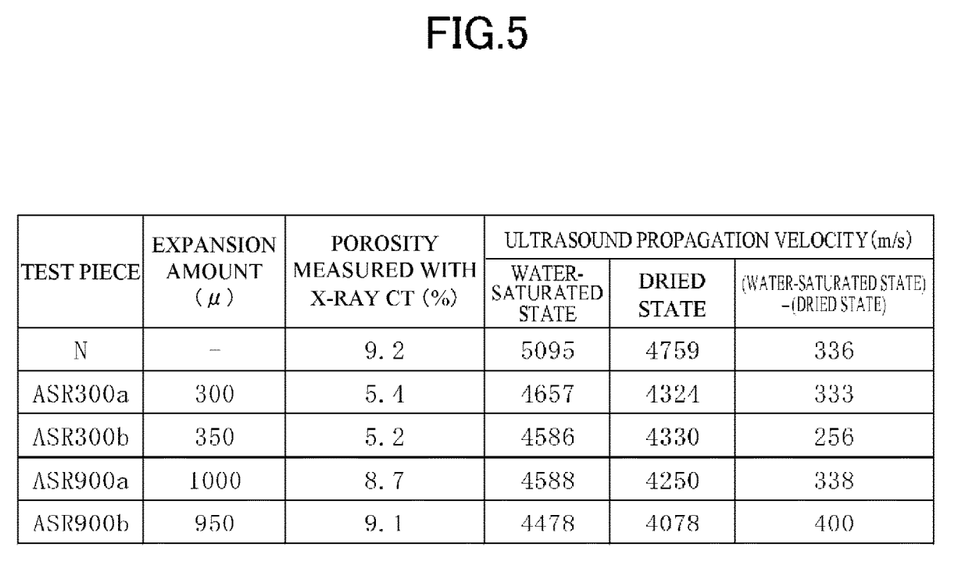
FIG. 5 is a table showing expansion amounts and other data of the test pieces in the present embodiment.

First, a configuration of the test piece TP will be described. In FIGS. 4 and 5, FIG. 4 is a list of test pieces used in this example, and FIG. 5 is a table showing expansion amounts and other data of the test pieces.

As shown in FIG. 4, in this example, five test pieces including test pieces N, ASR300a, ASR300b, ASR900a, and ASR900b (the last four test pieces were referred to as ASR series) were used as the test pieces.

Specifically, the test piece N was a 100 mm×100 mm×400 mm concrete block using a commonly used aggregate, and each of ASR series was a 75 mm×75 mm×400 mm concrete block using each reactive fine aggregate.

Regarding ASR series, a distance between measurement pins embedded in advance on both ends of each test piece was measured, and a change in the distance was divided by a base length of 400 mm, to calculate the expansion amount. Further, ASR300a, ASR300b used artificial cristobalite, ASR900a used andesite sand from Hokkaido, and ASR900b used Hokkaido andesite crushed sand. NaOH was added to the ASR series to achieve the alkali amounts shown in FIG. 4.

Material ages of all the test pieces were one year or older, and it was confirmed that the expansion amounts of ASR series had not changed since the end of an accelerating test until this test.

Further, regarding the ASR series, each piece having a thickness of about 50 mm was cut out from a portion near the center in the axial direction, and was used for the test. Regarding the test piece N, every surface was cut off by about 1 cm, and a piece having a thickness of about 50 mm was cut out from the rest of test piece N and was used for the test. Note that, in this example, a dried state was achieved by putting the test piece in a furnace set at 50° C., and a water-saturated state was achieved by putting the test piece in water. The dried state and the water-saturated state were each defined as a state where the mass of the test piece did not change.

Next, the following describes the results of an ultrasonic test and capturing of X-ray CT images, which are simple quality evaluation techniques, performed to determine denseness and void amounts of the test pieces, with reference to FIG. 5. The denseness and void amount are considered affecting the water permeation properties.

Ultrasound propagation velocities when ultrasound passed through each test piece in the width, height, and thickness directions were measured three times in each direction, for a total of nine times, and an average value of the velocities was defined as the ultrasound propagation velocity of the test piece. Note that, in consideration of influence of the water-content state, the measurements were performed in both of the dried state and the water-saturated state. A resonance frequency was 54 kHz, and a size of a probe was 6 cm in diameter. Further, in the case of the X-ray CT, the void amount was calculated from a 3D image created by stacking the CT images.

For CT imaging, an industrial X-ray CT device was used. To perform imaging, an X-ray tube voltage was 450 kV, a tube current was 1.55 mA, a resolution was 270 μm/pixel, and a slice thickness was 1 mm. To derive the void amount, CT images were modeled into volume data by CT data analysis software, the volume data was then subjected to binarization processing. Thereafter, when consecutive eight voxels were equal to or smaller than a threshold, a region of the eight voxels was determined as a void. In this way, voids of equal to or larger than sub-millimeter in size were extracted and were divided by a total volume, and the quotient was taken as a void ratio.

FIG. 5 shows the expansion amount and the void ratio of each test piece, the ultrasound propagation velocities of each test piece in the dried state and the water-saturated state, and the difference in the velocity caused by the difference in water-content state. The porosities of ASR300a and ASR300b were about 5%, and the porosities of ASR900a and ASR900b were about 9%. This shows the tendency of increase in void ratio with the increase in the expansion amount. The results of the ultrasound test show that, the ultrasound propagation velocities of the ASR series generally decrease with the increase in their expansion amounts.

On the other hand, regarding test piece N, the ultrasound propagation velocities in both of the dried state and the water-saturated state were the highest although the void ratio was 9.2%. The reason for this is thought that there is a difference in the influence of voids distributed in the test piece and cracks caused by alkali-silica reaction (ASR) on the velocity.

Next, the following describes a method for deriving the transmission image of the water permeated in each test piece (concrete piece) in the inspection device 1.

Specifically, the following three types of images are captured: a dark image captured without irradiation with a neutron beam; a direct image captured with irradiation with a neutron beam but with no test piece; and a sample image captured while a test piece is being irradiated with a neutron beam, and an image analysis is performed on the captured images with image processing software.

Imaging with neutrons involves a radiation noise, a noise due to pixel damage (outlier), and an offset that fluctuates depending on the ambient temperature or fluctuates before and after the irradiation with the beam in output images. Thus, a spatial filter is created to remove the noises, and an offset cancellation is performed in such a manner that the dark image is subtracted from the direct image and the sample image.

Then, a shading compensation is performed by dividing the sample image by the direct image so as to flatten the distribution of intensities of the neutron beam, thereby creating the transmission image.

Specifically, supposing that neutron intensities before and after entering of neutrons are respectively $l_{in}$ and $l_{out}$, the neutron transmittance T is expressed by $l_{out}/l_{in}$, and a logarithm $\ln(l_{out}/l_{in})$ of the transmittance is expressed by the following equation 1, which is a function proportional to an attenuation coefficient a and a thickness d. The attenuation coefficient a is constant for thermal neutrons, and the thickness d is a thickness of a substance for transmission.

$$\ln(l_{out}/l_{in}) = -ad \qquad \text{Equation 1}$$

Then, the transmission image of the water permeated, which is a difference (referred to as ΔT) between the images captured before the water absorption (time t=0) and after the water absorption (time t), was derived using the following equation 2.

$$\Delta T = -\ln(l_t/l_i=0) = a_w d_w \qquad \text{Equation 2}$$

In the above equation 2, $a_w$ is an attenuation coefficient of water per unit length, and $d_w$ is a thickness of the water permeated located in the transmission direction of neutrons.

Next, the following describes the evaluation of water permeation properties of concrete pieces.

Figure 6:
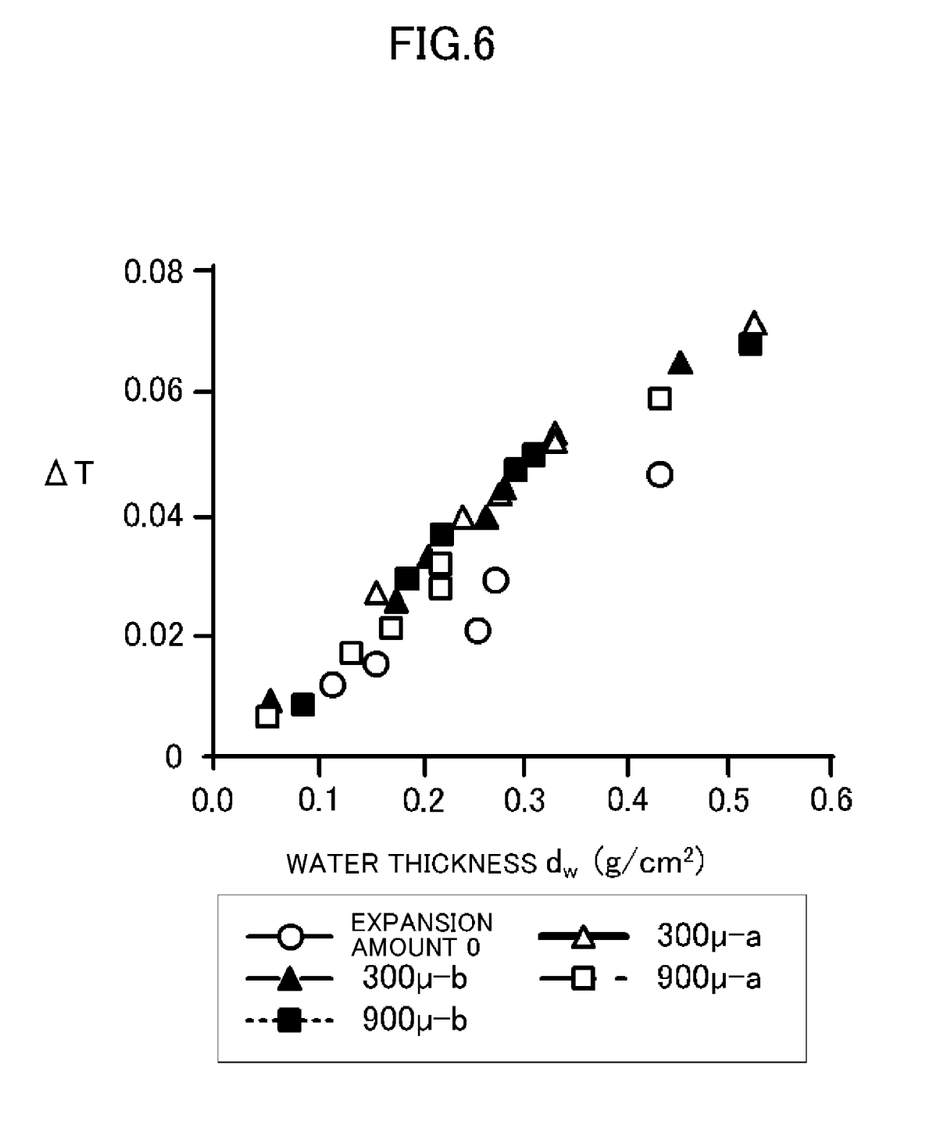
FIG. 6 is a relational graph between a water thickness and a transmittance difference in the present embodiment.

FIG. 6 is a relational graph between a water thickness and a transmittance difference. The graph shows the relationship between the water thickness $d_w$ and the transmittance difference ΔT before and after water absorption into each concrete piece. The water thickness is an average value and is calculated by dividing a water absorption amount measured by a scale by an entire area of a concrete surface on which the neutrons are incident.

As shown in FIG. 6, in the water absorbing process of all test pieces, the difference in the transmittance expands with the increase in water absorption amount, and a linear relationship between the thickness $d_w$ of water permeated and ΔT was confirmed. In the case of using the thermal neutrons, the change in ΔT with absorption of water in concrete is smaller with the increase in the thickness of the concrete caused by neutron diffusing, and water deeper inside the concrete is therefore more difficult to be seen.

For this reason, in the case of concrete thicker than 3 cm, quantitativity of the water thickness obtained from the transmission image may not be maintained. However, this example shows a linear relationship between the water thickness $d_w$ and the transmittance difference ΔT, and the permeation of water in concrete having a thickness of 5 cm can be evaluated if the water absorption amount is 0.5 g/cm².

Next, a temporal change in water permeation will be described.

Figure 7:
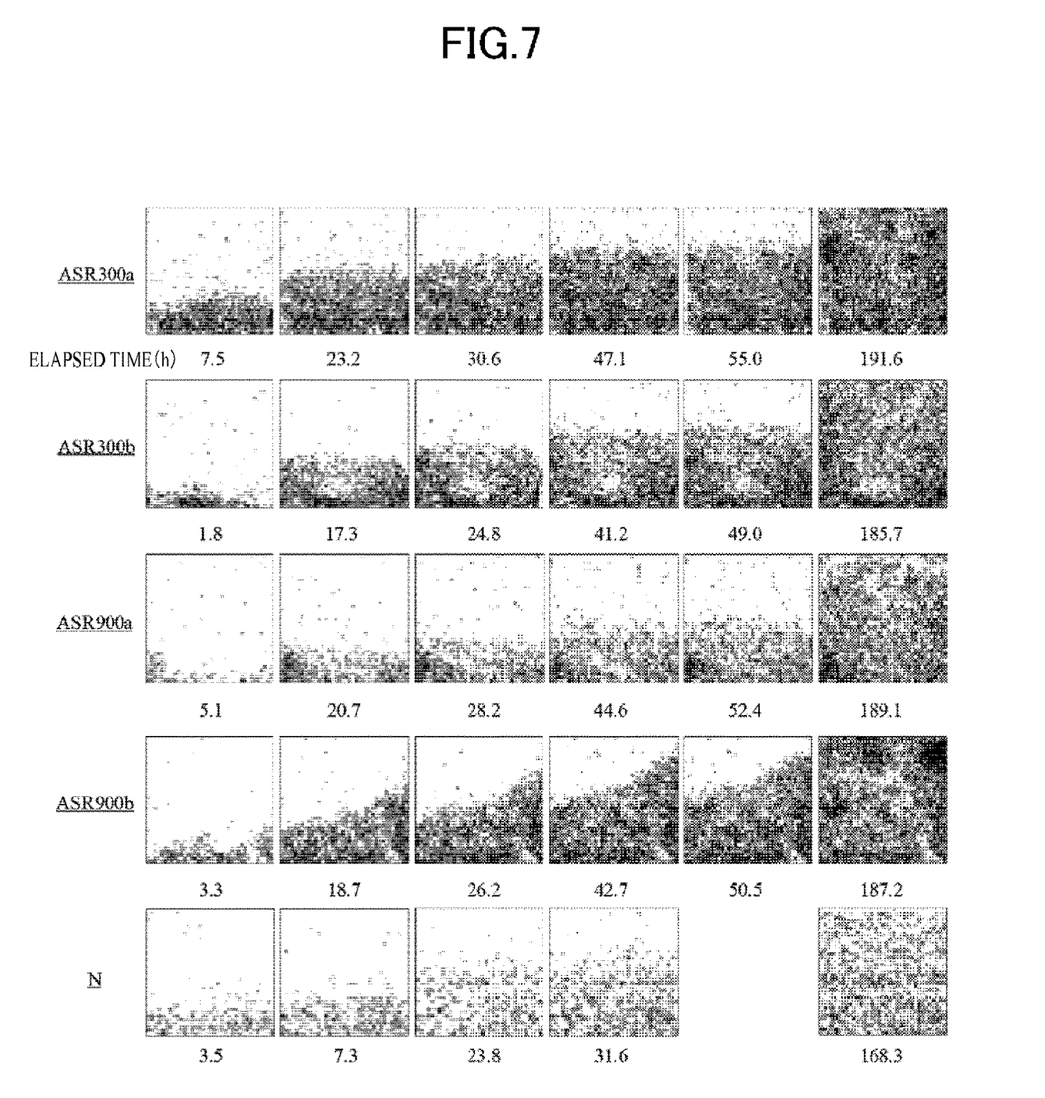
FIG. 7 shows transmission image charts of water permeated in a water absorbing process for five test pieces in the present embodiment.

FIG. 7 shows transmission image charts of water permeated into the five test pieces in the water absorbing process. In each chart, the difference ΔT in neutron transmittance before and after water absorption is displayed in gradation in gray scale. A resolution (dimensions of one pixel) is 1.8 mm×1.8 mm. Portions shown by the shadow represent water permeated, and it is shown that the amount of existing water is larger with the increase in depth of the shadow. Note that pixels having low transmittance are discretely distributed in the images. These pixels are caused as variations regardless of the presence of water when two images are divided by a statistic error of neutrons. It can be confirmed from the images that water permeation regions expand with time.

Specifically, for the test piece ASR900b, it can be confirmed that water permeation progresses non-uniformly. For each of the test pieces ASR300b and ASR900a, portions in which water permeation does not progress, which seems to be caused by coarse aggregate distribution, are seen, but after about one week, water is distributed in the entire test pieces.

Based on this fact, values of ΔT are accumulated in the horizontal direction for each pixel height, and a distribution of water in the height direction is plotted to evaluate a degree of water permeation involving non-uniformity.

Figure 8:
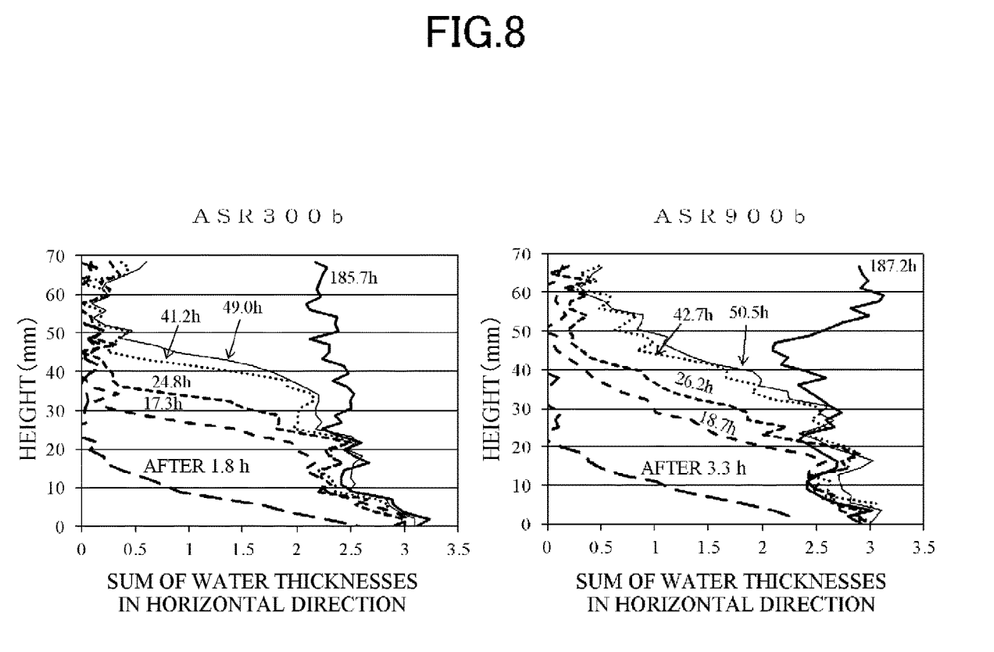
FIG. 8 shows graphs of temporal change in degree of water permeation into test pieces ASR300b and ASR900b.

FIG. 8 shows graphs of temporal change in the degree of water permeation into test pieces ASR300b and ASR900b. In each graph, the vertical axis represents the height (mm) of concrete, the horizontal axis represents the sum of water thicknesses in the horizontal direction, and the product of the value on the vertical axis and the value on the horizontal axis corresponds to the amount of water permeated.

In each graph, in portions at a height equal to or lower than 20 mm, the degree of water permeation after 25 hours have elapsed was the same as the degree of water permeation after 8 days have elapsed, and it is confirmed that water has been already saturated. Further, the test piece ASR900b shows a larger change in the degree of water permeation in the height direction than test piece ASR300b, it is considered that this larger change is caused by the non-uniform water permeation shown in the transmission images of FIG. 7.

Figure 9:
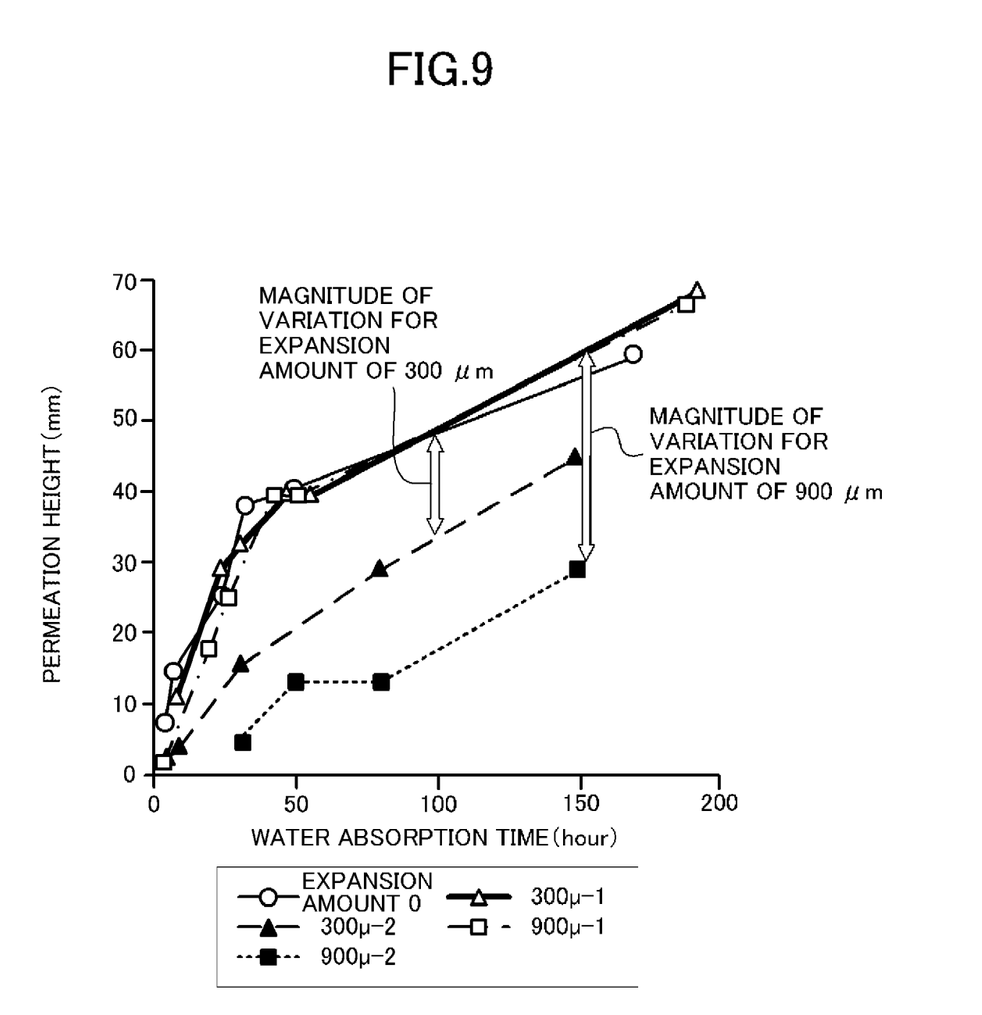
FIG. 9 is a graph showing temporal change in water permeation height of each of the test pieces.

FIG. 9 is a graph showing temporal change in water permeation height of each test piece. The water permeation height (mm) can be defined by, for example, a peak height or average height of the water distribution in the transmission images shown in FIG. 7, or alternatively can be defined by a height at a changing point of the water thickness at the degree of water permeation shown in FIG. 8, or by another value.

As shown in FIG. 9, the difference of change in water permeation height between test pieces ASR900a and ASR900b showing the expansion amount of about 300 p is larger than the difference of change in water permeation height between test pieces ASR300a and ASR300b showing the expansion amounts of about 900 p. In other words, a magnitude of variation in water permeation rate tends to be larger with the increase in the expansion amount.

Figure 10:
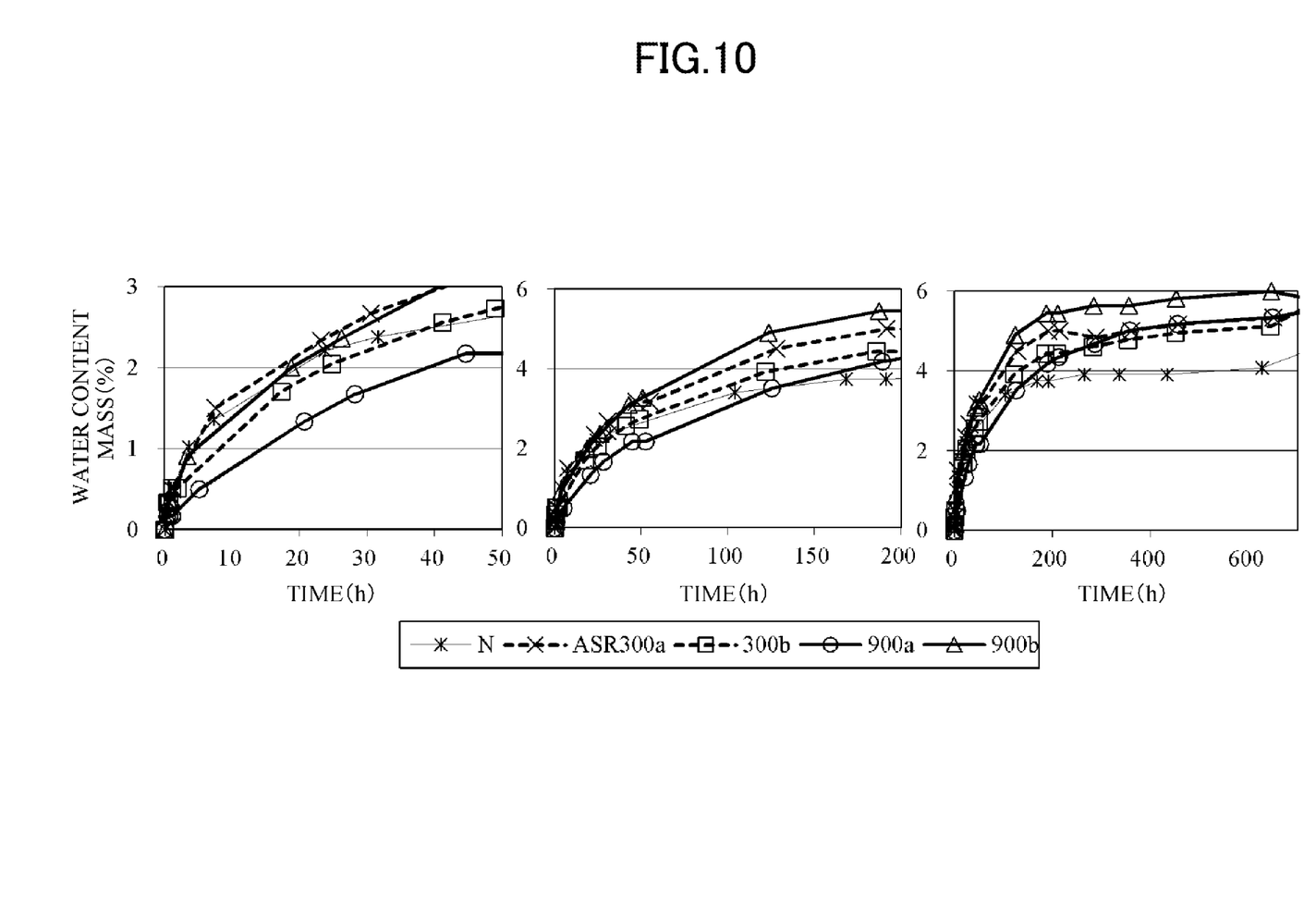
FIG. 10 shows graphs of temporal change in water content mass.

FIG. 10 shows graphs of temporal change in water content mass (obtained by dividing the water absorption amount by the weight of the test piece in the dried state). When 50 hours have elapsed since start of water absorption, the amounts of change in water content mass shows ASR900b>300a>300b>N>900a. This demonstrates that the respective changes in water content of the test pieces ASR900a and ASR900b showing the expansion amounts of about 900 p are a minimum and a maximum, which are two opposite extremes.

The result shows that the test piece ASR900a absorbed less water than the other test pieces and have a small water permeation region for the permeation properties shown in FIG. 8. The water content masses measured when 700 hours have elapsed show ASR900b>ASR900a>ASR300a>ASR300b>N. The result demonstrates that the test piece N, which is sound without occurrence of alkali-silica reaction, has the smallest water content mass. The test piece ASR900a shows a larger change in the water content mass after 50 hours than the other four test pieces, and reaches the water content mass next to that of ASR900b after 700 hours have elapsed.

On the other hand, the test piece ASR900b showing a maximum change in water content mass shows the lowest ultrasound propagation velocities in both of the water-saturated state and the dried state and a high void ratio in results of the ultrasonic test and X-ray CT imaging described above. This fact leads to an expectation that the test piece ASR900b is a test piece having the lowest quality and the lowest denseness among the five test pieces.

The test piece ASR900b has a maximum change in the water content mass since the start of water absorption and has non-uniform permeation properties. This is considered because differences in parameters such as the degree of deterioration, the mixing amount, and the material used appear as a macro movement of water. It is therefore understood that water permeation properties differ even when the expansion amounts are almost the same. The results of the five test pieces revealed that a non-uniform void structure in the height direction and horizontal direction, formed by expansion strain, causes differences in the temporal change in water content mass (water absorption rate) and in the distribution of water permeated.

This example demonstrated that by the evaluation of water permeation properties of the four test pieces with occurrence of alkali-silica reaction and the sound test piece, using the transmission images obtained with a compact accelerator-driven neutron source, the expansion amounts of the test pieces can be estimated. Accordingly, such a non-destructive inspection method more accurately evaluate the deterioration of a test piece such as a concrete piece on the basis of a water-content state of the test piece.

One embodiment of the present disclosure has been described above, but an aspect of the present disclosure is not limited to the foregoing embodiment.

For example, concrete pieces are used as test pieces in the above embodiment and example, but the present invention can be applied to other structures.

Although, in the above embodiment and example, the evaluation is performed on the basis of the transmission images obtained by transmission imaging of test pieces with a neutron source, but another type of radiation source may be used. For example, electromagnetic waves may be used to capture transmission images. However, the use of neutrons as in the embodiment and example is advantageous in that water can be detected with high sensitivity even when test pieces contain heavy metals such as iron, lead, and copper.

DESCRIPTION OF REFERENCE CHARACTERS

1 Inspection Device
2 Compact Accelerator-Driven Neutron Source
3 Detector
4 Test Piece Support
10 Power Supply
11 Linear Accelerator
12 Target Station
13 Irradiator
20 Aluminum Container

The invention claimed is:
1. A non-destructive inspection method comprising:
   a water absorbing or drying step of changing a water-content state of a test piece from a dried state or a water-saturated state;
   a transmission image capturing step of irradiating, with a radiation, the test piece absorbed water or dried for a predetermined time in the water absorbing or drying step and capturing a transmission image created by visualizing the radiation passed through the test piece; and
   an evaluation step of evaluating the test piece on the basis of a volume change of the test piece correlating with the water-content state of the test piece determined from the transmission image captured in the transmission image capturing step.

2. The non-destructive inspection method of claim 1, wherein the test piece is concrete.

3. The non-destructive inspection method of claim 2, wherein
   the radiation used in the transmission image capturing step is a neutron.

4. The non-destructive inspection method of claim 2, wherein
   the water-content state of the test piece determined from the transmission image in the evaluation step includes non-uniformity of a water permeation height.

5. The non-destructive inspection method of claim 2, wherein
   the water-content state of the test piece determined from the transmission image in the evaluation step includes a variation of a water permeation rate into the test piece.

6. The non-destructive inspection method of claim 2, wherein
   the water-content state of the test piece determined from the transmission image in the evaluation step includes a time differential of a water absorption rate of the test piece.

7. The non-destructive inspection method of claim 1, wherein
   the radiation used in the transmission image capturing step is a neutron.

8. The non-destructive inspection method of claim 7, wherein
   the water-content state of the test piece determined from the transmission image in the evaluation step includes non-uniformity of a water permeation height.

9. The non-destructive inspection method of claim 7, wherein
   the water-content state of the test piece determined from the transmission image in the evaluation step includes a variation of a water permeation rate into the test piece.

10. The non-destructive inspection method of claim 7, wherein
    the water-content state of the test piece determined from the transmission image in the evaluation step includes a time differential of a water absorption rate of the test piece.

11. The non-destructive inspection method of claim 1, wherein
    the water-content state of the test piece determined from the transmission image in the evaluation step includes non-uniformity of a water permeation height.

12. The non-destructive inspection method of claim 11, wherein the water-content state of the test piece determined from the transmission image in the evaluation step includes a variation of a water permeation rate into the test piece.

13. The non-destructive inspection method of claim 11, wherein
the water-content state of the test piece determined from the transmission image in the evaluation step includes a time differential of a water absorption rate of the test piece.

14. The non-destructive inspection method of claim 1, wherein
the water-content state of the test piece determined from the transmission image in the evaluation step includes a variation of a water permeation rate into the test piece.

15. The non-destructive inspection method of claim 14, wherein
the water-content state of the test piece determined from the transmission image in the evaluation step includes a time differential of a water absorption rate of the test piece.

16. The non-destructive inspection method of claim 1, wherein
the water-content state of the test piece determined from the transmission image in the evaluation step includes a time differential of a water absorption rate of the test piece.

* * * * *